United States Patent [19]

Richter et al.

[11] 4,400,549

[45] Aug. 23, 1983

[54] HYDROFORMYLATION OF OLEFINICALLY UNSATURATED COMPOUNDS

[75] Inventors: Wolfgang Richter, Ludwigshafen; Rudolf Kummer, Frankenthal; Kurt Schwirten, Ludwigshafen, all of Fed. Rep. of Germany

[73] Assignee: BASF Aktiengesellschaft, Fed. Rep. of Germany

[21] Appl. No.: 324,277

[22] Filed: Nov. 23, 1981

[30] Foreign Application Priority Data

Dec. 9, 1980 [DE] Fed. Rep. of Germany ....... 3046355

[51] Int. Cl.³ ............................................. C07C 45/50
[52] U.S. Cl. .................................... 568/454; 562/522; 562/521; 568/909
[58] Field of Search ....................... 568/454, 909, 882; 562/517, 522

[56] References Cited

U.S. PATENT DOCUMENTS 4,159,999  7/1979  Stautzenberger .................. 568/454
4,258,214  3/1981  Bahrmann et al. ................. 568/454

Primary Examiner—Werren B. Lone
Attorney, Agent, or Firm—Keil & Witherspoon

[57] ABSTRACT

A process for hydroformylating olefinically unsaturated compounds by means of rhodium/triphenylphosphine/carbonyl complexes formed in situ from rhodium acetate, triphenylphosphine and carbon monoxide, wherein the hydroformylation reaction is preceded by a starting phase in which the mixture of the hydroformylation medium, the triphenylphosphine and rhodium acetate is heated at from 90° to 120° C. under a $CO/H_2$ pressure of from 5 to 20 bar and the acetic acid liberated is discharged from the reactor in gaseous form in a stream of CO and $H_2$, until virtually no more acetic acid can be detected in this gaseous discharge.

3 Claims, No Drawings

HYDROFORMYLATION OF OLEFINICALLY UNSATURATED COMPOUNDS

The present invention relates to an improved process for hydroformylating olefinically unsaturated compounds (also called olefins in the text which follows) by means of rhodium/triphenylphosphine/carbonyl complexes produced in situ from rhodium acetate.

Apart from the improvement according to the invention, this process is generally known from numerous publications and does not require more detailed explanation.

The improvement according to the invention is based on the observation that, when rhodium acetate and triphenylphosphine are used, the active complex forms relatively slowly under the conditions of the synthesis. Since the olefin conversion increases with the amount of active catalyst, this means that complete conversion is achieved only after an operating time of some days. In contrast, if the finished complex $H.Rh(CO)(PPh_3)_3$ (Ph=phenyl) is used from the beginning, no such induction period occurs.

It is an object of the present invention to suppress the induction period in the hydroformylation of olefins by means of $Rh/PPh_3/CO$ complexes formed in situ from Rh acetate and $PPh_3$.

We have found that this object is achieved and that there is no induction period in the hydroformylation of olefinically unsaturated compounds by means of complexes formed in situ from rhodium acetate, triphenylphosphine and carbon monoxide if the hydroformylation reaction is preceded by a starting phase in which the mixture of the hydroformylation medium, the triphenylphosphine and rhodium acetate is heated at from 90° to 120° C. under a $CO/H_2$ pressure of from 5 to 20 bar and the acetic acid liberated is discharged from the reactor in gaseous form in a stream of CO and $H_2$, until virtually no more acetic acid can be detected in this gaseous discharge.

This starting phase, which only takes from about 2 to 8 hours, can also be described, in brief, as embracing all the hydroformylation measures, with the exception of the introduction of olefin. It can therefore be concluded that, surprisingly, formation of the active catalyst complex is favored if no olefin is present.

The hydroformylation medium advantageously consists of high-boiling hydroformylation by-products such as esters, acetals and aldol condensation products.

Since such products cannot yet have been formed in the starting phase, they must be obtained from earlier or parallel production runs of this type. If these products are not available, it is possible to use other relatively high-boiling inert solvents, such as diols and diol-esters, e.g. 2,2,4-trimethylpentane-1,3-diol monoisobutyrate. Per liter, the hydroformylation medium also contains from 2 to 120 g of triphenylphosphine and from 100 to 500 mg of rhodium, initially in salt form and later in coordinated form. When all the rhodium has been converted into the complex form, the olefins can be reacted under a pressure of an approximately equimolar mixture of CO and $H_2$ of from 5 to 30 bar at from 80° to 150° C., to give the corresponding aldehydes or mixtures of the corresponding isomeric aldehydes.

Since the hydroformylation following the catalyst activation according to the invention has no effect on this activation, the hydroformylation reaction of course does not depend on the nature of the olefins, i.e. the process is suitable as an intermediate stage for the hydroformylation of any olefin. The process is of particular importance in the case of hydroformylation of ethylene, propylene and the $C_8$-$C_{12}$-alkenes.

The aldehydes, as well as the alcohols, formed as products can be removed from the reactor in gaseous form in a conventional manner, together with the CO, $H_2$ and unreacted olefin. After the gas has been condensed and the aldehydes have been separated off, the olefin and most of the CO and $H_2$ are returned to the reactor as recycle gas.

This recycle gas procedure is also employed during this starting phase according to the invention, except that in this case the alcohol, which originates from the alcoholic Rh acetate solution, and, in particular, the acetic acid liberated are discharged instead of the aldehydes and the olefin.

If the starting materials are relatively high-boiling olefins and the products are therefore relatively high-boiling aldehydes, the recycle gas procedure may be less advantageous because of the relatively low partial pressure of these compounds than removal of liquid reaction mixture from the reactor and subsequent working up in a conventional manner. In that case, the recycle gas procedure is used only in the starting phase.

The alcohols which can be used for preparing the Rh acetate solutions are chiefly methanol and ethanol. The concentration of Rh acetate in the solutions is preferably from 1 to 10% by weight.

The acetic acid which is split off during complex formation according to the invention and is discharged with the recycle gas can be detected in the recycle gas in a conventional manner, for example by gas chromatography.

EXAMPLE

The initial period of hydroformylation of propylene by means of Rh catalysts was investigated with the aid of a test apparatus which was filled to the extent of 60% by volume with a mixture of 95% by weight of high-boiling hydroformylation products and 5% by weight of triphenylphosphine, the propylene conversion being determined under the following conditions: A (for comparison): The Rh was employed as a 5% strength by weight methanolic solution of Rh acetate and was in the reactor at the start of the hydroformylation.

| | |
|---|---|
| $CO/H_2$ ratio (molar) | 1:1 |
| Total pressure | 15 bar |
| Temperature | 110° C. |
| Rh concentration | 150 mg/kg of reaction medium |

B (for comparison): The Rh was used as a 5% strength by weight toluene solution of the complex $H.Rh(CO)(PPh_3)_3$ and was in the reactor at the start of the hydroformylation. The reaction conditions were as those in (A). C (according to the invention): The Rh was used as in (A), and the mixture was subjected to Rh-complex formation (starting phase) under the conditions in (A), but with no propylene being fed in. After 4.5 hours, no more acetic acid could be detected in the off-gas, so that the hydroformylation according to (A) was then carried out.

The results of experiments (A)–(C) are given in the following Table.

| Operating time t [h] (no starting phase) | Propylene conversion after t hours [%] | | |
|---|---|---|---|
| | A | B | C |
| 2 | 58 | 95 | 89 |
| 6 | 63 | 93 | 90 |
| 12 | 75 | 96 | 90 |
| 24 | 82 | 95 | 92 |
| 48 | 84 | 94 | 92 |
| 96 | 85 | 92 | 91 |

The experimental results show that, in contrast to case B and case C, the catalyst in case A had not achieved its full activity of about 90% even after 4 days.

The use of the finished Rh complex (case B) indeed provides the advantage of a high activity, which is even somewhat greater than that in case C at the start, but against this, the troublesome, separate preparation of the Rh complex is required. In comparison, the procedure in experiment C is considerably more economical.

We claim:

1. A process for hydroformylating olefinically unsaturated compounds by means of rhodium/triphenylphosphine/carbonyl complexes formed in situ from rhodium acetate, triphenylphosphine and carbon monoxide, wherein the hydroformylation reaction is preceded by a starting phase in which the mixture of the hydroformylation medium, the triphenylphosphine and rhodium acetate is heated at from 90° to 120° C. under a $CO/H_2$ pressure of from 5 to 20 bar and the acetic acid liberated is discharged from the reactor in gaseous form in a stream of CO and $H_2$, until virtually no more acetic acid can be detected in this gaseous discharge.

2. In a process for hydroformylating olefinically unsaturated compounds by means of rhodium/triphenylphosphine/carbonyl complexes formed in situ from rhodium acetate, triphenylphosphine and carbon monoxide, the improvement comprising: preceding the hydroformylation reaction with a starting phase wherein a mixture of the hydroformylation medium, triphenylphosphine and rhodium acetate is heated at from 90° to 120° C. under a $CO/H_2$ pressure of from 5 to 20 bar and the acetic acid liberated is discharged from the reactor in gaseous form in a stream of CO and $H_2$, until virtually no more acetic acid can be detected in this gaseous discharge, and thereafter passing the olefinically unsaturated compound into the reaction medium.

3. The process of claim 2 wherein the olefinically unsaturated compound is an olefin selected from the group consisted of ethylene, propylene and the $C_8-C_{12}$-alkenes.

* * * * *